United States Patent [19]
Kikuchi et al.

[11] Patent Number: 5,700,392
[45] Date of Patent: Dec. 23, 1997

[54] ANTIFERROELECTRIC LIQUID CRYSTAL COMPOSITION

[75] Inventors: Katsuhide Kikuchi, Kariya; Hitoshi Hayashi, Okazaki; Akira Takeuchi; Kenji Takigawa, both of Nishio, all of Japan

[73] Assignee: Nippon Soken, Inc., Aichi, Japan

[21] Appl. No.: 406,326

[22] Filed: Mar. 16, 1995

[30] Foreign Application Priority Data

Mar. 16, 1994 [JP] Japan .................................. 6-045902

[51] Int. Cl.$^6$ .................. C09K 19/12; C09K 19/20; C09K 19/52; C09K 19/34
[52] U.S. Cl. .................... 252/299.01; 252/299.6; 252/299.61; 252/299.66; 252/299.65; 252/299.67
[58] Field of Search ................. 252/299.66, 299.6, 252/299.01, 299.65, 299.67, 299.61

[56] References Cited

U.S. PATENT DOCUMENTS

| | | | |
|---|---|---|---|
| 4,576,732 | 3/1986 | Isogai et al. ................. | 252/299.65 |
| 4,754,051 | 6/1988 | Sasaki et al. ................. | 560/8 |
| 4,921,632 | 5/1990 | Nakamura et al. ............ | 252/299.1 |
| 4,961,874 | 10/1990 | Takeuchi et al. ............. | 252/299.6 |
| 5,046,823 | 9/1991 | Mori et al. .................... | 359/56 |
| 5,110,498 | 5/1992 | Suzuki et al. ................ | 252/299.66 |
| 5,151,213 | 9/1992 | Reiffenrath et al. ........... | 252/299.6 |
| 5,171,471 | 12/1992 | Suzuki et al. ................ | 252/299.61 |
| 5,184,847 | 2/1993 | Suzuki et al. ................ | 252/299.65 |

(List continued on next page.)

FOREIGN PATENT DOCUMENTS

| | | |
|---|---|---|
| 330491 | 8/1989 | European Pat. Off. . |
| 339987 | 11/1989 | European Pat. Off. . |
| 0517504A1 | 12/1992 | European Pat. Off. . |
| 0525737A1 | 2/1993 | European Pat. Off. . |
| 0562627A1 | 9/1993 | European Pat. Off. . |
| 582 468 | 2/1994 | European Pat. Off. . |
| 0582519A1 | 9/1994 | European Pat. Off. . |
| 1-139551 | 6/1989 | Japan . |
| 1213390 | 8/1989 | Japan . |
| 1316339 | 12/1989 | Japan . |
| 1316367 | 12/1989 | Japan . |
| 2-28128 | 1/1990 | Japan . |
| 2-69440 | 3/1990 | Japan . |
| 6271852 | 9/1994 | Japan . |

OTHER PUBLICATIONS

Nishiyama et al., "Effect of Size of the Lateral Substituent at the Chiral Centre on the Stability of Some Chiral Smectic Liquid–Crystalline Phases" Journal of Materials Chemistry 3(1993)No. 2, Cambridge, GB, pp. 149–159.
Suzuki et al., "New Fluorine–Containing Ferroelectric Liquid Crystal Compounds Containing Tristable Switching" Liquid Crystals 6(1989) No.2, London, GB, pp. 167–174.
Japanese Journal of Applied Physics, vol. 27, No. 5, May 1988, pp. L729–L732, May 5, 1988.
Mol. Cryst. Liq. Cryst., 1977, vol. 40, pp. 33–48.

*Primary Examiner*—C. H. Kelly
*Attorney, Agent, or Firm*—Cushman Darby & Cushman IP Group of Pillsbury Madison & Sutro LLP

[57] ABSTRACT

An antiferroelectric liquid crystal composition comprising a liquid crystal composition having the chiralsmectic $C_A$ phase and a compound represented by the formula (I) shown below:

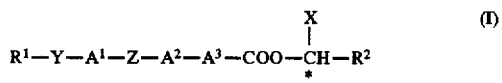

wherein X is —$CH_3$, —$CF_3$ or —$C_2H_5$; $R^1$ and $R^2$ are straight-chain or branched alkyl radicals having 3 to 14 and 3 to 10 carbon atoms respectively; Y represents a single bond, or —O—, —CO—, —COO— or —OCO— radical; Z represents —COO—, —C≡C— or —$CH_2CH_2$— radical; and $A^1$, $A^2$ and $A^3$ independently represent a six membered ring including benzene rings, cyclohexane rings, pyridine rings, and pyrimidine rings, at least one hydrogen of which six membered rings may be replaced by a fluorine atom, chlorine atom, bromine atom, cyano group, nitro group, methyl group, ethyl group or methoxy group.

5 Claims, 3 Drawing Sheets

U.S. PATENT DOCUMENTS

| | | | |
|---|---|---|---|
| 5,204,020 | 4/1993 | Suzuki et al. | 252/299.67 |
| 5,262,086 | 11/1993 | Suzuki et al. | 252/299.65 |
| 5,316,694 | 5/1994 | Murashino et al. | 252/299.61 |
| 5,330,678 | 7/1994 | Okabe et al. | 252/299.62 |
| 5,344,586 | 9/1994 | Suzuki et al. | 252/299.64 |
| 5,352,382 | 10/1994 | Johno | 252/299.65 |
| 5,356,562 | 10/1994 | Greenfield et al. | 252/299.63 |
| 5,374,375 | 12/1994 | Yui et al. | 252/299.65 |
| 5,378,392 | 1/1995 | Murashino et al. | 252/299.01 |
| 5,378,396 | 1/1995 | Yui et al. | 252/299.65 |
| 5,393,460 | 2/1995 | Okabe | 252/299.65 |
| 5,417,885 | 5/1995 | Suzuki et al. | 252/299.65 |
| 5,534,190 | 7/1996 | Johno et al. | 252/299.65 |

ANTIFERROELECTRIC LIQUID CRYSTAL COMPOSITION

BACKGROUND OF THE INVENTION

1. Field of the Invention

This invention relates to a liquid crystal composition. Particularly this invention relates to a liquid crystal composition having an ability to display an antiferroelectric (chiralsmectic $C_A$, hereinafter abbreviated to "$SmC_A^*$") phase. More particularly, this invention relates to an antiferroelectric liquid crystal composition suitable for use in a liquid crystal indication element.

2. Description of the Related Art

Recently, liquid crystal displays have become widely used as an indication element, due to their reduced thickness, light weight, low power consumption etc. However, most of these displays use TN (Twisted Nematic) type displays comprising a nematic liquid crystal. Since the driving of the indication method of the TN type is based on the anisotropy of the dielectric constant of the liquid crystal, the speed of response is slow, and an improvement is required.

In contrast, liquid crystal devices comprising chiralsmectic C (hereinafter abbreviated as "SmC*") liquid crystals, which are ferroelectric and were discovered by Meyer et al., have high response speeds and memory characteristics. Thus, in order to utilize these characteristics, applications of these ferroelectric liquid crystals to a device have been intensely researched. However, the good orientation and memory characteristics required for this indication method are difficult to realize in practice. For example, the cell has a problem that it is sensitive to external shocks etc., and it has many problems to be solved.

On the other hand, recently, an antiferroelectric phase (hereinafter abbreviated as "$SmC_A^*$ phase") has been discovered by Chandani et al. which shows three stable states on the lower temperature side of said SmC* phase. This antiferroelectric liquid crystal shows a thermodynamically stable phase wherein dipoles are arranged in antiparallel in every adjacent layer, and exhibits an electric field-induced phase transition between the antiferroelectric phase and the ferroelectric phase which is characterized by a clear threshold and double hysteresis in response to applied voltage. Investigation on new indication methods utilizing this switching behavior has begun.

In case of applying the switching characteristics of the antiferroelectric phase to a liquid crystal display, although it is not impossible to manufacture a liquid crystal cell by using a composition only containing antiferroelectric liquid crystal, it is not always preferable from the viewpoint of the temperature range showing the three stable states, the threshold voltage, crystallizing temperature, orientatability, etc.

SUMMARY OF THE INVENTION

In view of the above, an object of the present invention is to provide an antiferroelectric liquid crystal composition which has a low threshold voltage and low driving voltage.

This invention is an antiferroelectric liquid crystal composition comprising a liquid crystal composition having the chiralsmectic $C_A$ phase and a compound represented by the formula (I) shown below:

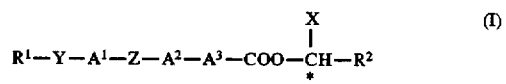

wherein X is $-CH_3$, $-CF_3$ or $-C_2H_5$; $R^1$ and $R^2$ are straight-chain or branched alkyl radicals having 3 to 14 and 3 to 10 carbon atoms respectively; Y represents a single bond, or $-O-$, $-CO-$, $-COO-$ or $-OCO-$ radical; Z represents $-COO-$, $-C\equiv C-$ or $-CH_2CH_2-$ radical; and $A^1$, $A^2$ and $A^3$ independently represent a six membered ring including benzene ring, cyclohexane ring, pyridine ring, pyrimidine ring, at least one hydrogen of which six membered ring may be replaced by fluorine atom, chlorine atom, bromine atom, cyano group, nitro group, methyl group, ethyl group or methoxy group etc.

DESCRIPTION OF THE PREFERRED EMBODIMENT

Figure 1:
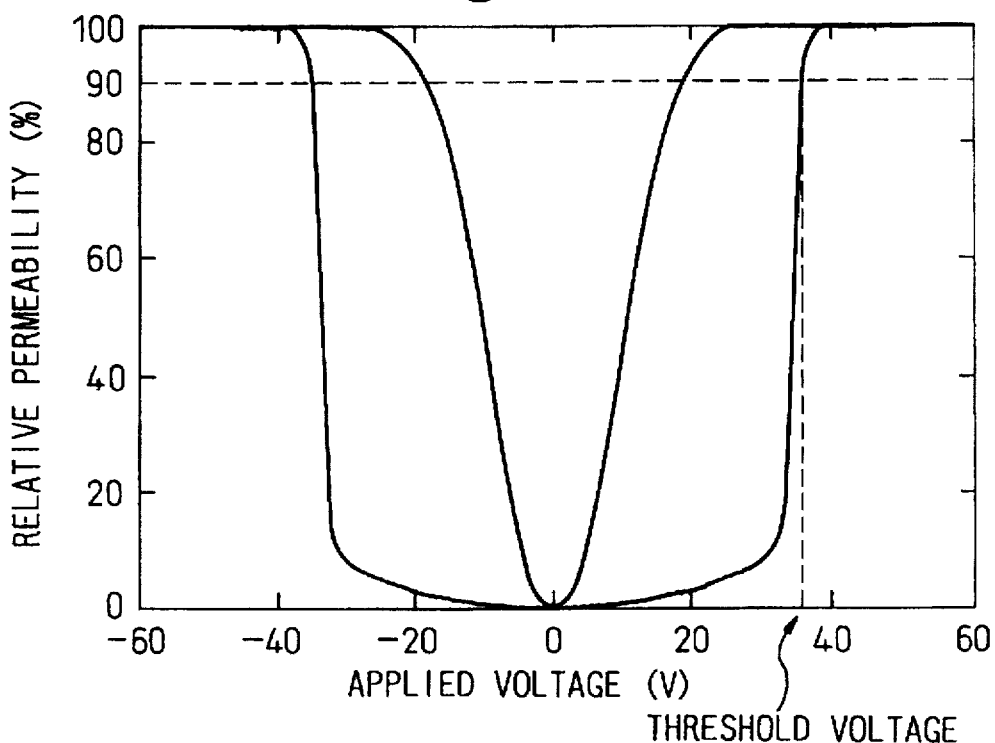
FIG. 1 is a graph of a double hysteresis curve obtained by applying a chopping wave of 1 Hz, and measuring the strength of a transmitted light under a crossed Nicols.

The antiferroelectric liquid crystal composition having chiralsmectic $C_A$ phase preferably contains at least one compound represented by the formula (II) below:

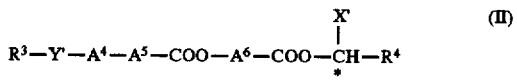

wherein X' is $-CH_3$, $-CF_3$ or $-C_2H_5$; $R^3$ and $R^4$ are straight-chain or branched alkyl radicals having 3 to 14 and 3 to 10 carbon atoms respectively; Y' represents a single bond, or $-O-$, $-CO-$, $-COO-$ or $-OCO-$ radical; and $A^4$, $A^5$ and $A^6$ independently represent a six membered ring including benzene rings, cyclohexane rings, pyridine rings, and pyrimidine rings, at least one hydrogen of which six membered ring may be replaced by a fluorine atom, chlorine atom, bromine atom, cyano group, nitro group, methyl group, ethyl group or methoxy group.

In the composition of a liquid crystal composition having $C_A$ phase and a compound represented by the formula (I), it is preferable that the proportion of the liquid crystal composition having the $C_A$ phase is 50 to 99 wt % and the proportion of the compound is 1 to 50 wt %, based on the total weight of the liquid crystal composition having the $C_A$ phase and the compound. If the proportion of the former is less than 50 wt %, the temperature range of the antiferroelectric phase of the composition is extremely reduced. On the other hand, if the proportion is greater than 99 wt %, the low voltage driving characteristics of the composition become poor.

In the above formula (I), $A^1$, $A^2$ and $A^3$ is preferably

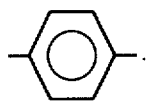

In the above formula (I), X is preferably —$CH_3$.

In the above formula (I), Y is preferably a single bond.

The compound represented by the formula (I) can be prepared as follows. First, a method of preparing the representative compound represented by the following formula (II) of the above compound is illustrated.

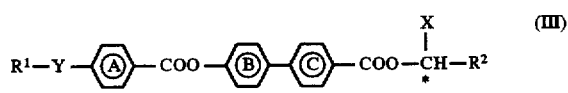

In the formula (III), $R^1$, $R^2$, X and Y are as defined for the chemical formula (I), and

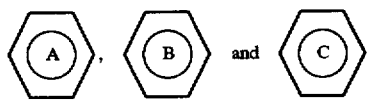

are all benzene rings, and hereinafter called benzene ring A, B and C, respectively.

Hereinafter the synthesis of this compound will be shown. In the chemical formulae hereinafter described, $R^1$, $R^2$, X and Y have the same meaning as above, and also

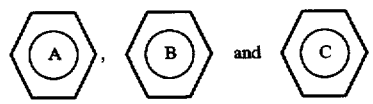

have the same meaning as above.

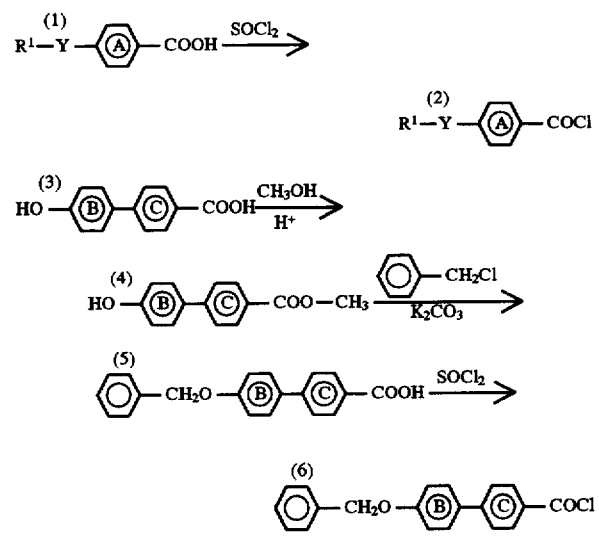

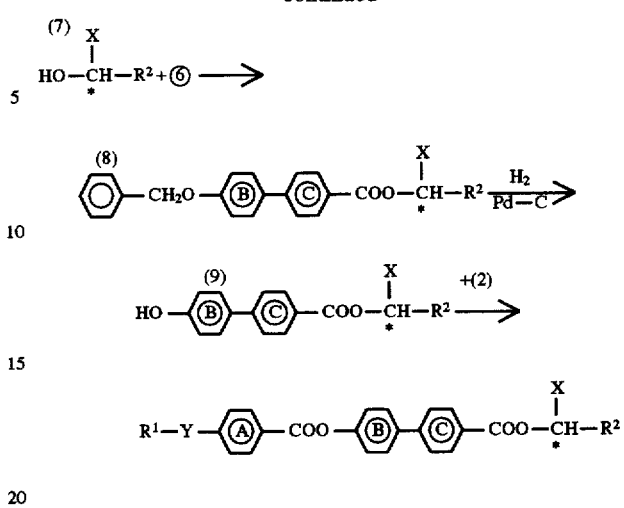

First, thionyl chloride is made to act on a compound (1), to obtain an acid chloride (2). Then, methanol is made to act on a compound (3) to form a methyl ester (4), thereafter benzyl chloride and potassium chloride are made to act on the compound (4) to obtain a compound (5). Then, thionyl chloride is made to act on the compound (5) to form an acid chloride (6). Then, a compound (7) is made to act on the compound (6) to obtain an ester compound (8). The obtained ester (8) is converted to a compound (9) by hydrogen addition under pressurized hydrogen using palladium carbon as a catalyst. Finally, compound (9) and compound (2) are reacted to obtain the objective compound (10).

In the above compound represented by the formula (II) and the compounds in the course of synthesis of the compound represented by the formula (II), each benzene ring A, B and C can independently be replaced by another six membered ring such as a cyclohexane ring, pyridine ring or pyrimidine ring, at least one hydrogen atom of which may be replaced by the above-mentioned fluorine atom, chlorine atom, bromine atom, cyano group, nitro group, methyl group, ethyl group or methoxy group etc.

Hereinafter, this invention will be illustrated by examples.

Example 1, Comparative Example 1

Using compounds No. 1 to 5 shown in Table 1, liquid crystal composition A (Comparative Example 1) and B (Example 1) was made. The composition A is a liquid crystal composition having a chiralsmectic $C_A$ phase, and compound No. 5 is one of the compounds represented by the formula (I).

TABLE 1

| Compound No. | Constitutional Formula (All R Modification) |
|---|---|
| 1 | $C_8H_{17}O$—⬡—⬡—COO—⬡—COO$\overset{*}{C}H(CF_3)C_6H_{13}$ |
| 2 | $C_{10}H_{21}O$—⬡—⬡—COO—⬡—COO$\overset{*}{C}H(CF_3)C_6H_{13}$ |
| 3 | $C_{10}H_{21}$—⬡—⬡—COO—⬡—COO$\overset{*}{C}H(CF_3)C_6H_{13}$ |
| 4 | $C_{11}H_{23}$—⬡—⬡—COO—⬡—COO$\overset{*}{C}H(CF_3)C_6H_{13}$ |
| 5 | $C_8H_{17}$—⬡—COO—⬡—⬡—COO$\overset{*}{C}H(CF_3)C_6H_{13}$ |

TABLE 2

| | Composition | |
|---|---|---|
| Composition A (Comp. Ex. 1) | Compound No. 1 | 5 wt % |
| | Compound No. 2 | 20 wt % |
| | Compound No. 3 | 30 wt % |
| | Compound No. 4 | 45 wt % |
| Composition B (Example 1) | Composition A | 80.0 wt % |
| | Compound No. 5 | 20.0 wt % |

Figure 2:
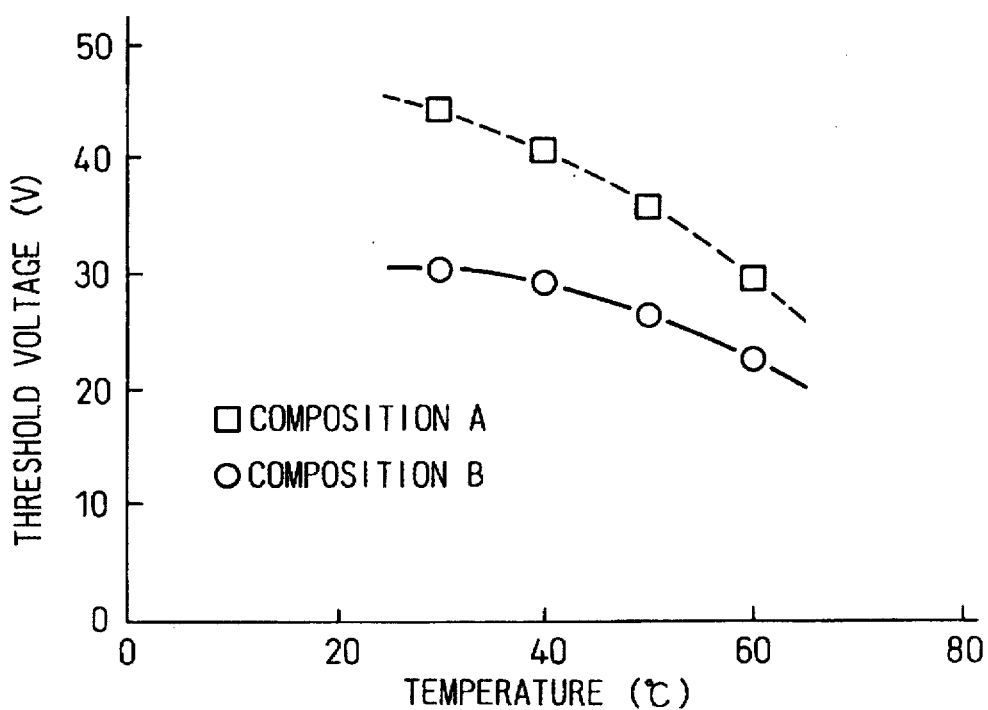
FIG. 2 is a graph showing a temperature-threshold characteristic curve of the liquid crystal compositions of Example 1 and Comparative Example 1.

The liquid crystal compositions A and B were injected into the liquid crystal cells (gap: 2 μm) which were orientation treated by rubbing. After injection, the cell was heated to a temperature where the liquid crystal becomes an isotropic liquid, and thereafter cooled to room temperature at a rate of 2° C./min. to obtain an antiferroelectric liquid crystal element. To this element, a chopping wave of 1 Hz was applied, and the strength of a transmitted light was measured under a crossed Nicols, thereby a double hysteresis curve as shown in FIG. 1 was obtained. In this hysteresis, a voltage where the relative transmittance at the time of increasing the voltage is 90% is defined as the threshold voltage. The threshold voltages of the compositions A and B were determined at various temperatures and were plotted against the temperatures, thereby results were obtained as shown in FIG. 2. The threshold temperature of the composition B is lower than that of the composition A. The driving voltage of the composition A for phase transition from SmC$_A$* phase to electric field induced SmC* phase at 30° C. was 23 V/μm. On the other hand, the driving voltage of the composition B was 16 V/μm which is lower than that of the composition A.

The phase transition temperatures of the compositions A and B are shown in Table 3. As is shown in Table 3, the upper limit temperatures of the SmC$_A$* phases for the composition A and B are 74° C. and are the same, which shows that although the compound No. 5 is blended into the composition A (the composition B), the upper limit temperature of the SmC$_A$* phase does not decrease.

TABLE 3

| Liquid Crystal Material | Phase Transition Temperature, °C. | | | | |
|---|---|---|---|---|---|
| | Cry. | SmC$_A$* | SmC* | SmA | I$_{so}$ |
| Composition A (Comp. Ex. 1) | — | . 74 | | . | 78 |
| Composition B (Example 1) | — | . 74 | . 77 | . | 90 |

The above composition A, which consists of all antiferroelectric liquid crystal compounds, has a high threshold voltage, thus has a poor applicability. When the compound represented by the formula (I) is added to the composition A to form composition B, the threshold voltage of the composition B decreases sharply and nevertheless shows a high speed response. Further, a liquid crystal composition showing a SmC$_A$* phase having a wide temperature range can be produced.

Example 2, Comparative Example 2

Liquid crystal composition C (Comparative Example 2) and D (Example 2) shown in the Table 5 below were prepared using the compounds No. 6 to 10 shown in the Table 4 below and the compounds No. 3 and 5 shown in the Table 1 above.

TABLE 4

| Compound No. | Constitutional Formula (All R Modification) |
|---|---|
| 6 | $C_8H_{17}O$—⟨F⟩—⟨⟩—COO—⟨⟩—COOCH(CF$_3$)C$_8$H$_{17}$* |
| 7 | $C_9H_{19}O$—⟨F⟩—⟨⟩—COO—⟨⟩—COOCH(CF$_3$)C$_8$H$_{17}$* |
| 8 | $C_8H_{17}$—⟨⟩—⟨⟩—COO—⟨⟩—COOCH(CF$_3$)C$_8$H$_{17}$* |
| 9 | $C_9H_{19}$—⟨⟩—⟨⟩—COO—⟨⟩—COOCH(CF$_3$)C$_8$H$_{17}$* |
| 10 | $C_{10}H_{21}$—⟨⟩—⟨⟩—COO—⟨⟩—COOCH(CF$_3$)C$_8$H$_{17}$* |
| 11 | $C_9H_{19}$—⟨⟩—COO—⟨⟩—⟨⟩—COOCH(CH$_3$)C$_6$H$_{13}$* |
| 12 | $C_{10}H_{21}$—⟨⟩—C≡C—⟨⟩—⟨⟩—COOCH(CH$_3$)C$_5$H$_{11}$* |
| 13 | $C_{10}H_{21}$—⟨⟩—C$_2$H$_4$—⟨⟩—⟨⟩—COOCH(CH$_3$)C$_5$H$_{11}$* |

TABLE 5

| | Composition | |
|---|---|---|
| Composition C (Comp. Ex. 2) | Compound No. 3 | 30 wt % |
| | Compound No. 6 | 10 wt % |
| | Compound No. 7 | 10 wt % |
| | Compound No; 8 | 15 wt % |
| | Compound No. 9 | 20 wt % |
| | Compound No. 10 | 15 wt % |
| Composition D (Example 2) | Composition C | 80.0 wt % |
| | Compound No. 5 | 20.0 wt % |

Figure 3:
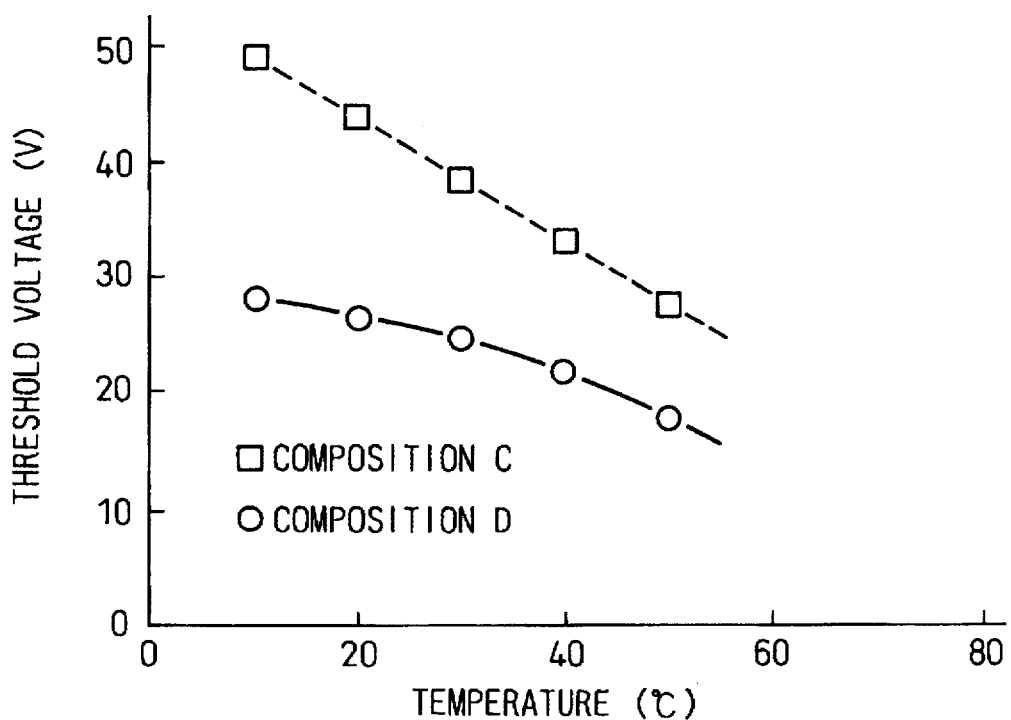
FIG. 3 is a graph showing a temperature-threshold characteristic curve of the liquid crystal compositions of Example 2 and Comparative Example 2.

Measuring the threshold voltages for the compositions C and D, the threshold voltages were plotted against the measuring temperatures, to give the results shown in FIG. 3. The threshold temperature of the composition D is lower than that of the composition C. The driving voltage of the composition C at 30° C. is 19 V/μm. In comparison to this, the driving voltage of the composition D is 12 V/μm which is far lower than that of the composition C.

Phase transition temperatures of the compositions C and D are shown in Table 6. The composition D shows a higher upper limit temperature of the SmC$_A$* phase than that of the composition C, so that this invention provides a composition having a broader temperature range of the SmC$_A$* phase.

TABLE 6

| Liquid Crystal Material | Phase Transition Temperature | | | |
|---|---|---|---|---|
| | Cry. | SmC$_A$* | SmC* | SmA | I$_{so}$ |
| Composition C (Comp. Ex. 2) | — | • | 60 | • | 66 |
| Composition D (Example 2) | — | • | 62 | • | 78 |

Example 3, Comparative Example 1

Liquid composition E (Example 3) shown in Table 7 below was manufactured using the composition A shown in the above Table 2 and the compound No. 11 shown in Table 4.

Figure 4:
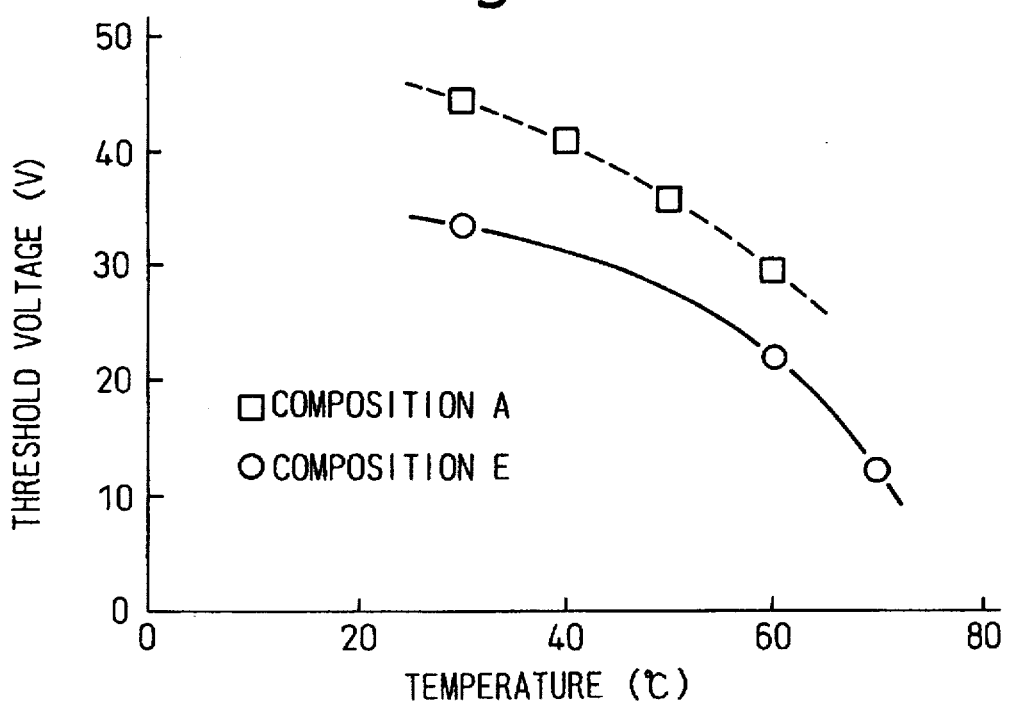
FIG. 4 is a graph showing a temperature-threshold characteristics curve of the liquid crystal compositions of Example 3 and Comparative Example 1.

Measuring the threshold voltages for the compositions A and E, the threshold voltages were plotted against the measuring temperatures, to give the results shown in FIG. 4. The threshold temperature of the composition E is lower than that of the composition A. The driving voltage of the composition A at 30° C. is 23 V/μm. In comparison to this, the driving voltage of the composition E is 17 V/μm which is far lower than that of the composition A.

Phase transition temperatures of the composition E are shown in Table 8. Generally, mixing of a compound having no SmC$_A$* phase with a liquid composition having the SmC$_A$* phase lowers the upper limit temperature of the SmC$_A$* phase of the resulting composition. Although the compound No. 11 has no SmC$_A$* phase, the upper limit temperature of the SmC$_A$* phase of the composition E is the same as that of the composition A.

Example 4, Comparative Example 1

Liquid composition F (Example 4) shown in Table 7 below was manufactured using the composition A shown in the above Table 2 and the compound No. 12 shown in Table 4.

Figure 5:
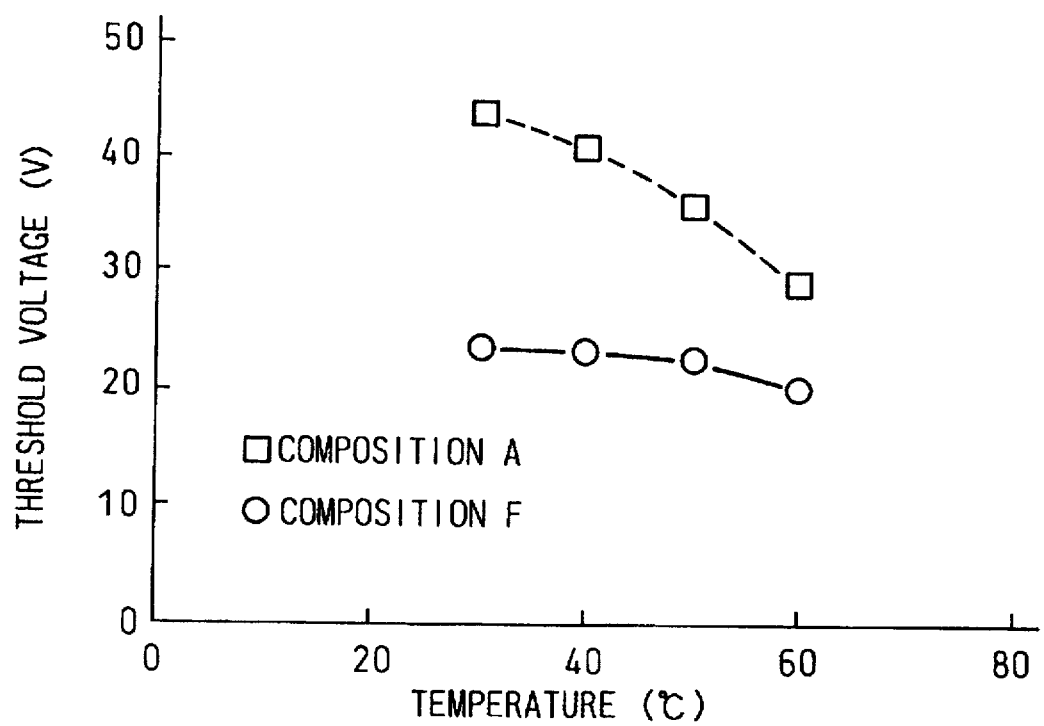
FIG. 5 is a graph showing a temperature-threshold characteristic curve of the liquid crystal compositions of Example 4 and Comparative Example 1.

Measuring the threshold voltages for the compositions A and F, the threshold voltages were plotted against the measuring temperatures, to give the results shown in FIG. 5. The threshold temperature of the composition F is lower than that of the composition A. The driving voltage of the composition A at 30° C. is 23 V/μm. In comparison to this, the driving voltage of the composition F is 12 V/μm which is far lower than that of the composition A.

Phase transition temperatures of the composition F are shown in Table 8. The upper limit temperature of the SmC$_A$* phase of the composition F is higher than that of the composition A.

Example 5, Comparative Example 1

Liquid composition G (Example 5) shown in Table 7 below was manufactured using the composition A shown in the above Table 2 and the compound No. 13 shown in Table 4.

Figure 6:
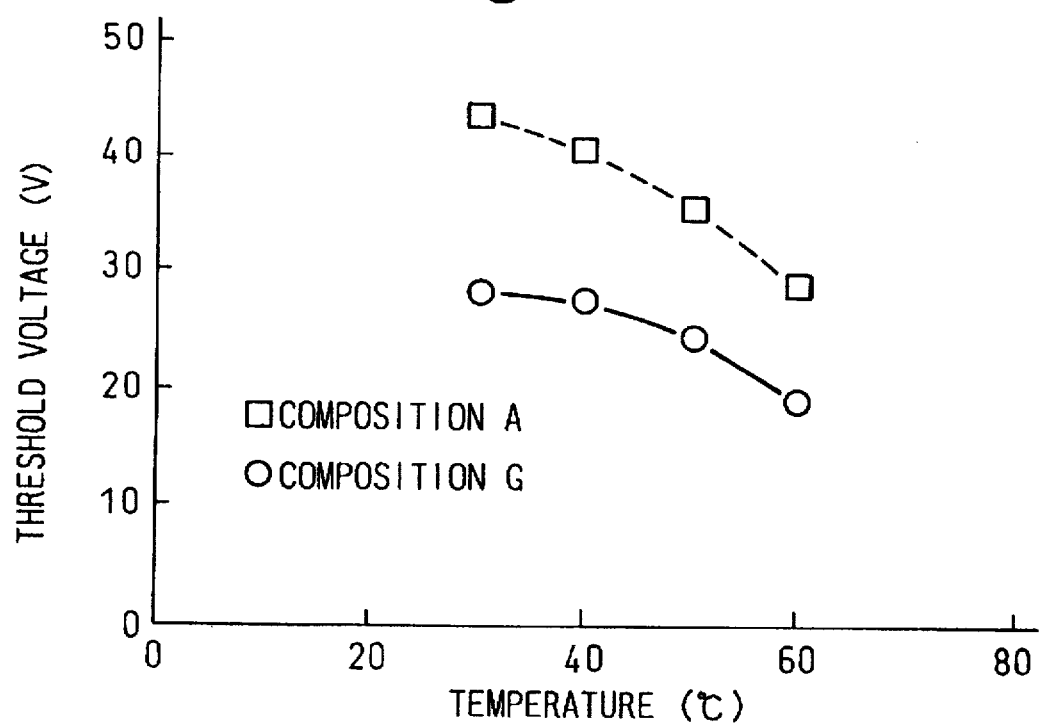
FIG. 6 is a graph showing a temperature-threshold characteristics curve of the liquid crystal compositions of Example 5 and Comparative Example 1.

Measuring the threshold voltages for the compositions A and G, the threshold voltages were plotted against the measuring temperatures, to give the results shown in FIG. 6. The threshold temperature of the composition G is lower than that of the composition A. The driving voltage of the composition A at 30° C. is 23 V/μm. In comparison to this, the driving voltage of the composition G is 14 V/μm which is far lower than that of the composition A.

Phase transition temperatures of the composition G are shown in Table 8. Generally, mixing of a compound having no SmC$_A$* phase with a liquid composition having the SmC$_A$* phase lowers remarkably the upper limit temperature of the SmC$_A$* phase of the resulting composition. Although the compound No. 13 has no SmC$_A$* phase, the upper limit temperature of the SmC$_A$* phase of the composition G only decreased by 5° C. in comparison to that of the composition A.

TABLE 7

|  | Composition |  |
| --- | --- | --- |
| Composition E (Example 3) | Composition A | 80.0 wt % |
|  | Compound No. 11 | 20.0 wt % |
| Composition F (Example 4) | Composition A | 80.0 wt % |
|  | Compound No. 12 | 20.0 wt % |
| Composition G (Example 5) | Composition A | 80.0 wt % |
|  | Compound No. 13 | 20.0 wt % |

TABLE 8

| Liquid Crystal Material | Phase Transition Temperature, °C. | | | |
| --- | --- | --- | --- | --- |
|  | Cry. | SmC$_A$* | SmC* | SmA | I$_{so}$ |
| Composition E (Example 3) | — | . 74 | . | . 85 | |
| Composition F (Example 4) | — | . 78 | . 80 | . 89 | |
| Composition G (Example 5) | — | . 69 | . 71 | . 75 | |

This invention provides an antiferroelectric liquid crystal composition and liquid crystal element having low threshold voltage, ability to be driven at a low voltage and broad crystal temperature range.

I claim:

1. An antiferroelectric liquid crystal composition consisting essentially of:

50 to 99 wt % of a liquid crystal composition having an antiferroelectric phase and containing at least one compound represented by the formula (II) shown below:

$$R^3-Y'-A^4-A^5-COO-A^6-COO-\overset{X'}{\underset{*}{C}H}-R^4 \quad (II)$$

wherein X' is —CH$_3$, —CF$_3$ or —C$_2$H$_5$; R$^3$ and R$^4$ are straight chain or branched alkyl radicals having 3 to 14 and 3 to 10 carbon atoms respectively; Y' represents a single bond, or —O—, —CO—, —COO— or —OCO— radical; and A$^4$, A$^5$ and A$^6$ independently represent a six membered ring selected from the group consisting of benzene rings, cyclohexane rings, pyridine rings and pyrimidine rings, at least one hydrogen of which six membered ring may be replaced by a fluorine atom, chlorine atom, bromine atom, cyano group, nitro group, methyl group, ethyl group or methoxy group; and 1 to 50 wt % of a compound represented by the formula (I) shown below:

$$R^1-Y-A^1-Z-A^2-A^3-COO-\overset{X}{\underset{*}{C}H}-R^2 \quad (I)$$

wherein the wt % is based on the total weight of the liquid crystal composition having the antiferroelectric phase and the compound represented by the formula (I); X is —CH$_3$, —CF$_3$ or —C$_2$H$_5$; R$^1$ and R$^2$ are straight chain or branched alkyl radicals having 3 to 14 and 3 to 10 carbon atoms respectively; Y represents a single bond, or —O—, —CO—, —COO— or —OCO— radical; Z represents —COO—, —C≡C— or —CH$_2$CH$_2$— radical; and A$^1$, A$^2$ and A$^3$ independently represent a six membered ring selected from the group consisting of benzene rings, cyclohexane rings, pyridine rings and pyrimidine rings, at least one hydrogen of which six membered ring may be replaced by a fluorine atom, chlorine atom, bromine atom, cyano group, nitro group, methyl group, ethyl group or methoxy group.

2. The antiferroelectric liquid crystal composition according to claim 1, wherein each A$^1$, A$^2$ and A$^3$ is

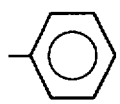
respectively.
3. The antiferroelectric liquid crystal composition according to claim 1, wherein X is —CH$_3$.
4. The antiferroelectric liquid crystal composition according to claim 1, wherein Y is a single bond.
5. The antiferroelectric liquid crystal composition according to claim 1, wherein each A$^1$, A$^2$ and A$^3$ is
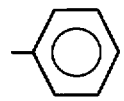
respectively; X is —CH$_3$; and Y is a single bond.
* * * * *